US008652470B2

(12) United States Patent
Hansen

(10) Patent No.: US 8,652,470 B2
(45) Date of Patent: *Feb. 18, 2014

(54) MONOCLONAL ANTIBODIES DIRECTED TO CD52

(75) Inventor: Genevieve Hansen, Del Mar, CA (US)

(73) Assignee: Vet Therapeutics, Inc., Del Mar, CA (US)

(*) Notice: Subject to any disclaimer, the term of this patent is extended or adjusted under 35 U.S.C. 154(b) by 222 days.

This patent is subject to a terminal disclaimer.

(21) Appl. No.: 13/040,170

(22) Filed: Mar. 3, 2011

(65) Prior Publication Data

US 2011/0217304 A1 Sep. 8, 2011

Related U.S. Application Data

(60) Provisional application No. 61/310,450, filed on Mar. 4, 2010.

(51) Int. Cl.
A61K 39/395 (2006.01)
(52) U.S. Cl.
USPC .................... 424/133.1; 530/387.1
(58) Field of Classification Search
None
See application file for complete search history.

(56) References Cited

U.S. PATENT DOCUMENTS

| | | | |
|---|---|---|---|
| 5,760,185 A | 6/1998 | Kimachi et al. | |
| 5,852,183 A | 12/1998 | Maeda et al. | |
| 6,028,059 A | 2/2000 | Curiel et al. | |
| 6,468,738 B1 | 10/2002 | Kang et al. | |
| 7,342,110 B2 | 3/2008 | Hoffee et al. | |
| 7,531,628 B2 | 5/2009 | Beall | |
| 8,337,842 B2 * | 12/2012 | Hansen | 424/133.1 |
| 2002/0041847 A1 | 4/2002 | Goldenberg | |
| 2002/0165135 A1 | 11/2002 | McCall et al. | |
| 2003/0219433 A1 | 11/2003 | Hansen et al. | |
| 2003/0219861 A1 | 11/2003 | Rother et al. | |
| 2004/0181039 A1 | 9/2004 | Krah et al. | |
| 2005/0271662 A1 | 12/2005 | Beall | |
| 2006/0040325 A1 | 2/2006 | Wu et al. | |
| 2006/0134709 A1 | 6/2006 | Stavenhagen et al. | |
| 2006/0183195 A1 | 8/2006 | Lonberg et al. | |
| 2007/0004909 A1 | 1/2007 | Johnson | |
| 2007/0036799 A1 | 2/2007 | Stavenhagen et al. | |
| 2007/0141047 A1 | 6/2007 | McCall et al. | |
| 2008/0050370 A1 | 2/2008 | Glaser et al. | |
| 2008/0188401 A1 | 8/2008 | Cruwys | |
| 2008/0248529 A1 | 10/2008 | Carr et al. | |
| 2010/0061988 A1 | 3/2010 | Hansen | |
| 2011/0002917 A1 | 1/2011 | Hansen | |
| 2011/0217304 A1 | 9/2011 | Hansen | |

FOREIGN PATENT DOCUMENTS

| | | |
|---|---|---|
| EP | 0419858 | 4/1991 |
| WO | WO 01/94585 | 12/2001 |
| WO | WO 03/048208 | 6/2003 |
| WO | WO 03/060080 | 7/2003 |
| WO | WO 2004/003019 | 1/2004 |
| WO | WO 2006/126068 | 11/2006 |
| WO | WO 2010/027488 | 3/2010 |
| WO | WO 2010/110838 | 9/2010 |
| WO | WO 2011/109108 | 9/2011 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
GenBank Direct Submission AAL35304.1; Immunoglobulin Gamma Heavy Chain D [*Canis lupus* familiaris]; Nov. 26, 2011; <http://www.ncbi/nm/nih.gov/protein/AAL35304.1>.
International Search Report and Written Opinion of the International Searching Authority for International Application No. PCT/US2011/027094 mailed May 4, 2011.
UniProtKB Direct Submission QT8896. CD52_CANFA; Feb. 1, 1998; <http://www.ncbi.nlm.nih.gov/protein/3182945?sat=OLID&satkey=5321424>.
Babcock, et al. "Ligand Binding Characteristics of CXCR4 Incorporated into Paramagnetic Proteoliposomes" 276 (42): 3843-38440 (2001).
Chabanne, Manuscript available (2006) World Congress WSAVA/FECAWA/CSAWA, reprinted on www.IVIS.org; 456-459.
Chun, "Lymphoma: Which Chemotherapy Protocol and Why?" Topics in Companion Animal Medicine, 24 (3): 157-162 (2009).
Das et al., "Evolutionary dynamics of the immunoglobulin heavy chain variable region genes in vertebrates", 60: 47-55 (2008).
Das et al., "Evolutionary redefinition of immunoglobulin light chain isotypes in tetrapods using molecular markers" 105 (43): 16647-16652 (2008).
Ferrer, L., "Canine Atopic Dermatitis: Evidence Based Dermatology", Proceeding of the NAVC North American Veterinary Conference, Jan. 8-12, Orlando, Fl. (2005).
Gershwin, L., "Veterinary Autoimmunity: Autoimmune Diseases in Domestic Animals", Ann. N.Y. Acad Sci. 1109: 109-116 (2007).
Hale et al., "CD52 (CAMPATH-1)" J Biol Regul Homeost Agents 15: 386-91 (2001).
Mirzabekov et al., "Paramagnetic proteoliposomes containing a pure, native, and oriented seven-transmembrane segment protein, CCR5" Nat. Biotech. 18: 649-654 (2000).
Tang et al., "Cloning and characterization of cDNAs encoding four different canine immunoglobulin gamma chains" Vet. Imm. Immunopath. 80: 259-270 (2001).
Wilkerson et al., "Lineage differentiation of canine lymphoma/leukemia's and aberrant expression of CD molecules" Vet. Imm. And Immunopath. 106 (3-4): 179-96 (2005).
Withrow & MacEwen's, "Small Animal Clinical Oncology" (Ed. 4)), D. Vail and S. Withrow, Ed.s, Saunders Elsevier, St Louis, (2007).
Adamski, King and Demmer, "Expression of the Fc receptor in the mammary gland during lactation in the marsupial *Trichosurus vulpecula* (brushtail possum)", Mol Immunol 37: 435-444 (2000).

(Continued)

Primary Examiner — Sheela J Huff
(74) Attorney, Agent, or Firm — Hoxie & Associates LLC

(57) ABSTRACT

The invention provides antibody to canine or feline or equine antigens, e.g., canine CDS2, and methods of making and using antibodies as described.

19 Claims, No Drawings

(56) References Cited

OTHER PUBLICATIONS

Chaudhury, Mehnaz, Robinson, Hayton, Pearl and Roopenian. et al., "The major histocompatibility complex-related Fc receptor for IgG (FcRn) binds albumin and prolongs its lifespan", The Journal of Experimental Medicine 197: 315-322 (2003).

Cianga, Cianga, Cozma, Ward and Carasevici, "The MHC class I related Fc receptor, FcRn, is expressed in the epithelial cells of the human mammary gland", Hum Immunol 1152-1159 (2003).

Cianga, Medesan, Richardson, Ghetie and Ward, "Identification and function of neonatal Fc receptor in mammary gland of lactating mice," Eur J Immunol 29: 2515-2523 (1999).

Daeron, "Fc receptor biology. Annu Rev Immunol" 5:203-234, (1997).

Davis, Dennis, Odom, Gibson, Kimberly, Burrows, and Cooper MD Fc receptor homologs: newest members of a remarkably diverse Fc receptor gene family. Immunol Rev. 190: 123-136 (2002)—Abstract Only.

Davis, Ehrhardt, Leu, Hirand, Cooper (An extended family of Fc receptor relatives. Eur J Immunol (2005) 35: 674-680.

Mazza, et al. "Tissue Immunoglobulin G Subclasses Observed in Immune-mediated Dermatopathy, Deep Pyoderma and Hypersensitivity Dermatitis in Dogs", Vet. Sci. 58: 82-89 (1995).

Fayngerts, et al. "Species-specific Evolution of the FcR Family in Endothermic Vertebrates", Immunogenetics 59: 493-506 (2007).

Ghetie and Ward, "Multiple roles for the major histocompatibility complex class I-related receptor FcRn", Annu Rev Immunol 18: 739-766 (2000).

Helfand, Hank, Gan and Sondel. Lysis of Human Tumor Cell Lines by Canine Complement plus Monoclonal Antiganglioside Antibodies or Natural Canine Xenoantibodies. Cellular Immunology 167: 99-107 (1996).

Jubala et al. "CD20 Expression in Normal Canine B Cells and in Canine non-Hodgkin Lymphoma", Vet. Pathol. 42: 468-476 (2005).

Kacskovics, Wu, Simister, Frenyo and Hammarstrom, Cloning and characterization of the bovine MHC class I-like Fc receptor, J Immunol 164: 1889-1897 (2000).

Kim, Bronson, Hayton, Radmacher, Roopenian and Robinson et al., Albumin turnover: FcRn-mediated recycling saves as much albumin from degradation as the liver produces, Am J Physiol Gastrointest Liver Physiol (2005).

Lilliehöok, Johannisson, and Hakansson. Expression of adhesion and Fcgamma-receptors on canine blood eosinophils and neutrophils studied by anti-human monoclonal antibodies. Vet Immunol Immunopathol. 61: 181-93 (1998).

Maltais Lovering, Taranin, Colonna, Ravetch, Dalla-Favera, Burrows, Cooper, Davis New nomenclature for Fc receptor-like molecules. Nat Immunol 7: 431-432 (2006).

Mayer, Doleschall, Bender, Bartyik, Bosze and Frenyo et al., Expression of the neonatal Fc receptor (FcRn) in the bovine mammary gland, J Dairy Res 72 (Spec No. 107-112) (2005).

Mayer, Zolnai, Frenyo, Jancsik, Szentirmay and Hammarstrom et al., Localization of the sheep FcRn in the mammary gland, Vet Immunol Immunopathol 87: 327-330 (2002).

Mayer, Zolnai, Frenyo, Jancsik, Szentirmay and Hammarstrom et al., Redistribution of the sheep neonatal Fc receptor in the mammary gland around the time of parturition in ewes and its localization in the small intestine of neonatal lambs, Immunology 107: 288-296 (2002).

Mazza et al. "The Separation and Identification by Monoclonal Antibodies of Dog IgG Fractions", J. Imm. Meth. 161: 193-203 (1993).

MacCallum et al., "Antibody-antigen interactions: Contact Analysis and Binding Site Topography" (J. Mol. Biol. [1996] 262: 732-745).

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody" (The Journal of Immunology [2002] 169: 3076-3084).

Casset et al., "A Peptide Mimetic of an anti-CD4 Monoclonal Antibody by Rational Design" BBRC [2003] 307: 198-205).

Vajdos et al., "Comprehensive Functional Maps of the Antigen-binding Site of an Anti-ErbB2 Antibody Obtained with Shotgun Scanning Mutagenesis", (J. Mol. Biol. [2002] 320, 415-428).

Holm et al., "Functional Mapping and Single Chain Construction of the Anti-Cytokeratin 8 Monoclonal Antibody TS1", (Mol. Immunol. [2007] 44: 1075-1084).

Chen et al., "Selection and Analysis of an Optimized Anti-VEGF Antibody: Crystal Structure of an Affinity-matured Fab in complex with Antigen", (J. Mol. Bio. [1999] 293, 865-881).

Wu et al., "Humanization of a Murine Monoclonal Antibody by Simultaneous Optimization of Framework and CDR Residues", (J. Mol. Biol. [1999] 294, 151-162).

Brummell et al., "Probing the combining site of an anti-carbohydrate antibody by saturation-mutagenesis: role of the heavy-chain CDR3 residues", (Biochemistry [1993] 32: 1180-1187).

Kobayashi et al., "Trytophan H33 plays an important role in pyrimidine (6-4) pyrimidine photoproduct binding by a high-affinity antibody" (Protein Engineering [1999] 12: 879-844).

Burks et al., "In Vitro scanning saturation mutagenesis of an antibody binding pocket", (PNAS [1997] 94: 412-417).

Jang et al., "The structural basis for DNA binding by an anti-DNA autoantibody", (Molec. Immunol. [1998] 35: 1207-1217).

Brorson et al., "Mutational Analysis of Avidity and Fine Specificity of Anti-Levan Antibodies", (J. Immunol. [1999].

Colman, "Effects of amino acid sequence changes on antibody-antigen interactions", (Research in Immunol. [1994] 145: 33-36).

Ward et al., "Binding activities of a repertoire of single immunoglobulin variable domains secreted from *Escherichia coli*", (Nature [1989] 341: 544-546).

Smith-Gill et al., "Contributions of immunoglobulin heavy and light chains to antibody specificity for lysozyme and two haptens", (J. Immunol. [1987] 139: 4135-4144).

Kumar et al., "Molecular Cloning and Expression of the Fabs of Human Autoantibodies in *Escherichia coli*", (J. Biol. Chem. [2000] 275: 35129-35136).

Song et al., "Light Chain of Natural Antibody Plays a Dominant Role in Protein Antigen Binding", (Biochem. Biophys. Res. Comm. [2000] 268: 390-394).

Written Opinion of the International Searching Authority for International Application No. PCT/US2009/004997 mailed Feb. 17, 2010.

Phillips, Padilla, Dickerson, Lindstrom, and Helfand. Immunostimulatory effects of human recombinant interleukin-12 on peripheral blood mononuclear cells from normal dogs. Vet Immunol Immunopathol. 70: 189-201 (1999).

Ravetch and Kinet "Fc Receptors." Annu Rev Immunol 9: 457-492 (1991).

Wozna, et al., "The immunological. biochemical and molecular bases of canine senescence and carcinogenesis: a review", Veterinarni Medicina, 57 (7): 350-359 (2012).

Rodewald, R, pH-dependent binding of immunoglobulins to intestinal cells of the neonatal rat, J Cell Biol. 71: 666-669 (1976).

Sato, Teshima, Nakamura, Takagi, Sasaki, Sawada, and Kitani Canine mast cell activation via human IgG1 and IgG4. Int Arch Allergy Immunol. 135:154-60 (2004).

Schnulle and Hurley, Sequence and expression of the FcRn in the porcine mammary gland, Vet Immunol Immunopathol. (2003) 91: 227-231.

Simister and Mostov An Fc receptor structurally related to MHC class I antigens, Nature 337: 184-187 (1989).

Soergel, MacEwen, Vail, Potter, Sondel, and Helfand. The immunotherapeutic potential of activated canine alveolar macrophages and antitumor monoclonal antibodies in metastatic canine melanoma. J Immunother. 22: 443-53 (1999).

Kano et al., "Canine CD20 gene" Vet. Imm. Immunopath. 108: 265-268 (2005).

Rudikoff et al. (Proc. Nat'l. Acad. Sci. USA vol. 79, pp. 1979 (1982).

Maccoux, L.J., et al. "Expression profiling of select cytokines in canine osteoarthritis tissues" Vet. Immun. Immunopath. 118: 59-67 (2007).

Doom et al., "Immunopathological mechanisms in dogs with rupture of the cranial cruciate ligament" 125: 143-161 (2008).

(56) References Cited

OTHER PUBLICATIONS

Carter et al., "Canine rheumatoid arthritis and inflammatory cytokines" Vet. Immun. Immunopath. 69: 201-214 (1999).

Sutton, et al., "The contribution of synovium, synovial derived inflammatory cytokines and neuropeptides to the pathogenesis of osteoarthritis", Vet. J. 179: 10-24 (2009).

R&D Systems product literature for antibody AF2305 dated Jun. 9, 2006 and accessed Jun. 5, 2012.

R&D Systems product literature for antibody MAB16091 dated Jan. 24, 2005 and accessed Jun. 5, 2012.

Shin et al., "Studies of cocktail therapy with multiple cytokines for neoplasia or infectious disease of the dog I. cDNA cloning of canine IL-3 and IL-6", J. Vet. Sci. 2 (2): 115-120 (2001).

Extended European Search Report Issued Dec. 21, 2012 for EP application 09811845.8 (PCT/US2009004997).

Caldas et al., "Humanization of the anti-CD18Antibody 6.7: An Unexpected Effect of a Framework Residue in Binding to Antigen", Mol. Immunol., vol. 39, (2003), pp. 941-952.

Chien et al., "Significant Structural and Functional Change of An Antigen-Binding Site by a Distant Amino Acid Substitution: Proposal of a Structural Mechanism", Proc. Natl. Acad. Sci. USA, vol. 86, pp. 5532-5536, (Jul. 1989).

Dutra et al., "C-erbB-2 Expression and Nuclear Pleomorphism in Canine Mammary Tumors", Brazilian Journal of Medical and Biological Research, (2004), vol. 37, pp. 1673-1681.

Giusti et al., "Somatic Diversification of S107 from an Antiphosphocholine to an Anti-DNA Autoantibody is Due to a Single Base Change in its Heavy Chain Variable Region", Proc. Natl. Acad. Sci. USA, vol. 84, pp. 2926-2930, (May 1987).

Gussow et al., Humanization of Monoclonal Antibodies, Methods in Enzymology, vol. 203, pp. 99-121, (1991).

Mariuzza et al., "The Structural Basis of Antigen-Antibody Recognition", Ann. Rev. Biophys. Biophys. Chem. (1987), vol. 16, pp. 139-159.

Winkler et al., Changing the Antigen Binding Specificity by Single Point Mutations of an Anti-p24 (HIV-1) Antibody[1], 2000.

Day, M.J. et al., "Tissue Immunoglobin G Subclasses Observed in Immune-Mediated Dermatopathy, Deep Pyoderma and Hypersensitivity Dermatitis in Dogs.", Vet. Sci., vol. 58, pp. 82-89, (1995).

Gong, R., et al., "Engineered Human Antibody Constant Domains with Increased Stability", The Journal of Biological Chemistry, vol. 284, No. 21, pp. 14203-14210, (May 22, 2009).

Robinson, et al., "Albumin Turnover: FcRn-Mediated Recycling Saves as Much Albumin from Degradation as the Liver Produces.", Am. J. Physiol. Gastrointest. Liver Physiol., (2005).

International Search Report and Written Opinion of the Searching Authority [US] for International Application No. PCT/US2010/00666 Mailed Apr. 2, 2012.

Extended European Search Report completed Jun. 5, 2013 for European Application No. 10756449.4 (PCT/US2010/00666).

Extended European Search Report completed Jul. 10, 2013 for European Application No. 11751388.7 (PCT/US2011/027094).

\* cited by examiner

MONOCLONAL ANTIBODIES DIRECTED TO CD52

CROSS REFERENCE TO RELATED APPLICATIONS

This application claims the benefit of priority under 35 USC §119 of U.S. Provisional Application Ser. No. 61/310,450 filed Mar. 4, 2010, the disclosures of which are incorporated herein by reference.

FIELD OF THE INVENTION

This invention generally relates to monoclonal antibodies, including portions or variants, directed to CD52 for the treatment of diseases, e.g., in mammals and particularly in companion animals, such as dogs, cats and horses. More particularly, the invention provides antibody constructs, and antibodies encoded by the constructs, which react with CD52 and are useful for detection of targets, diagnosis of disease and treatment of companion animals. Further disclosed herein are methods for the treatment of leukocyte-related disorders in companion animals. These methods are based upon the administration of an anti-CD52 antibody or antibodies targeting the CD52 of a companion animal for the modulation of leukocytes.

BACKGROUND OF THE INVENTION

The use of immunoglobulins as therapeutic treatment for a variety of diseases and disorders is rapidly increasing because they have shown to be safe and efficacious therapeutic agents. Approved therapeutic monoclonal antibodies for human use include Trastuzumab (antigen: 180 kD, HER2/neu), Alemtuzumab (antigen: 21-28 kD, CD52), and Rituximab (antigen: 35 kD, CD20). Additional therapeutic proteins are in various phases of clinical development for humans for a variety of diseases with the majority targeting various forms of cancer and inflammatory-related diseases.

Antibodies target an antigen through its binding of a specific epitope on an antigen by the interaction with the variable region of the antibody molecule. At the same time, the constant region of the antibody may additionally recruit other cells or molecules for example to destroy the cell or protein to which the antibody is bound or trigger further immune reactions. Certain regions of the immunoglobulin constant domain may elicit antibody-mediated cytotoxicity (ADCC), complement-mediated cytotoxicity (CDC), phagocytosis, immediate hypersensitivity, regulation of the 1 g synthesis, and antigen presenting cells.

Whereas antibodies have been studied and developed in several mammalian species such as humans and mice, they have been significantly less studied in companion animals such as canine, feline, and equine mammals. Treatments to address veterinary immune and inflammatory conditions have been borrowed from drugs developed for humans, often with imperfect results and generally consist of drugs classified as small molecules including non-steroidal anti-inflammatory agents, analgesic agents, steroidal agents, immunosuppressive agents or anti-metabolites, and chemotherapeutic agents. The arsenal of veterinary medicine is thus limited when it comes to addressing immune conditions and cancer. Additional drawback of these treatments is that they generally only address symptoms and they are associated with serious side effects as large doses have to be administered repeatedly for a long period of time with cumulative effects that often tend to be worse than the disease itself.

There is a thus a need for improved and more specific treatments and biologic agents for use in animals, such as companion animals. Heterochimeric antibodies and antibodies having enhanced effector regions for use in treating companion animals are generally described in the Applicant's own international publications: US 2010/0061988A1 and US 2010/110838A2, the contents of each are incorporated herein by reference. There is still a need for highly specific antibodies which are not immunogenic in companion animals and which are effective to treat diseases characterized by overproliferation of CD52-positive cells in companion animals.

SUMMARY OF THE INVENTION

The invention provides therapeutic antibodies useful for veterinary application, particularly antibodies directed to canine or feline or equine CD52, for example canine CD52, together with methods of making such antibodies using optimized immunogenic constructs and methods treatment using such antibodies.

DETAILED DESCRIPTION OF THE INVENTION

It is to be understood that both the foregoing general description and the following detailed description are exemplary and explanatory only and are not restrictive of the invention, as claimed. It must be noted that, as used herein and in the appended claims, the singular forms include plural referents; the use of "or" means "and/or" unless stated otherwise. Thus, for example, reference to "a subject polypeptide" includes a plurality of such polypeptides and reference to "the agent" includes reference to one or more agents and equivalents thereof known to those skilled in the art, and so forth. Moreover, it must be understood that the invention is not limited to the particular embodiments described, as such may, of course, vary. Further, the terminology used to describe particular embodiments is not intended to be limiting, since the scope of the present invention will be limited only by its claims.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Unless otherwise defined, all technical and scientific terms used herein have the same meaning as commonly understood by one of ordinary skill in the art to which this invention belongs. Suitable methods and materials are described below, however methods and materials similar or equivalent to those described herein can be used in the practice of the present invention. Thus, the materials, methods, and examples are illustrative only and not intended to be limiting. All publications, patent applications, patents, and other references mentioned herein are incorporated by reference in their entirety. In case of conflict, the present specification, including definitions, will control.

Standard techniques may be used for recombinant DNA, oligonucleotide synthesis, tissue culture and transfection (e.g., electroporation, lipofection, etc.). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989); Mayer and Walker, Immunochemical Methods In Cell And Molecular Biology, Academic Press, London (1987); Borrebaeck, Antibody Engineering, 2nd ed., Oxford Univ. Press (1995); Roitt et al., Immunology 6$^{th}$ ed., Mosby (2001); All of the references cited above, as well as all references cited herein, are incorporated herein by reference in their entireties.

The present invention provides methods for engineering heterochimeric antibodies and/or fragments thereof suitable for administration to a subject for treatment of a disease. The terms "patient," "subject," and "individual," are used interchangeably herein, to refer to mammals, including, but not limited to, humans, murines, simians, felines, canines, equines, bovines, porcines, ovines, caprines, mammalian farm and agricultural animals, mammalian sport animals, and mammalian pets. In certain embodiments of the invention, the subject is a companion animal, such as a dog, cat or horse.

Heterochimeric antibodies engineered thereof are the result of the fusion of portion of the variable domain nucleotide sequences to constant region nucleotide sequences and the co-expression of these sequences to produce heterochimeric recombinant antibodies. Furthermore, the invention relates to the use of such heterochimeric antibodies and/or fragments thereof as immunotherapeutic agents for the treatment of disease in animals and as diagnostic agents.

Antibodies created according to the present invention offer several advantages, such as (i) reduced immunogenicity response upon repeated administration; (ii) increased potency mediated by an efficient recruitment of immune system responsible for effector functions in the targeted species; and (iii) increased half-life.

The present invention includes generation of antibodies and/or fragments thereof with the desired properties and their use in production. The antibodies from the present invention include a fragment of the variable region of an antibody derived from a species that is different than the one of the constant region. Thus, the antibodies and/or fragments thereof retain the specificities and high affinities with the desired effector functions in the target species.

The antibodies of the present invention in particular embodiments may recognize any therapeutic target suitable for antibody therapy, for example a tumor-related antigen, an allergy- or inflammation-related antigen, a cardiovascular disease-related antigen, an autoimmune disease-related antigen or a viral or bacterial infection-related antigen.

"Native antibodies" as used herein are usually glycoproteins of about 150,000 daltons, composed of two identical light chains and two identical heavy chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (variable region) ($V_H$) followed by a number of constant domains (constant regions). Each light chain has a variable domain at one end ($V_L$) and a constant domain at its other end; the constant domain of the light chain is aligned with the first constant domain of the heavy chain, and the light-chain variable domain is aligned with the variable domain of the heavy chain.

The "light chains" of antibodies from any vertebrate species can be assigned to one of two clearly distinct types, called kappa and lambda.

Depending on the amino acid sequence of the "constant domain" or "constant region" of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains corresponding to the different classes of immunoglobulins are called alpha, delta, epsilon, gamma, and mu, respectively.

The term "variable domain" refers to the fact that certain portions of the variable domains differ in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4). The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity (ADCC) and complement activation.

Papain digestion of antibodies produces two identical antigen-binding fragments, called "Fab" fragments, each with a single antigen-binding site, and a residual "Fc" fragment, whose name reflects its ability to readily crystallize. Pepsin treatment yields a binding cross-linking antigen.

"Fv" as used herein, refers to the minimum antibody fragment that contains a complete antigen-recognition and binding site. This region consists of a dimer of one heavy chain and one light chain variable domain.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other configurations of antibody fragments will also be well-known to the skilled artisan.

The term "antibody" is used herein in the broadest sense and specifically includes monoclonal antibodies (including full length monoclonal antibodies), polyclonal antibodies, multispecific antibodies (e.g., bispecific antibodies), and antibody fragments exhibiting the desired biological or functional activity. The desired biological or functional activity will include at least binding to a cognate antigen and may further include complement activation and/or other effector functions. By "full length antibody" herein is meant the structure that constitutes the natural biological form of an antibody, including variable and constant regions.

"Antibody fragments" or "antigen-binding moiety" comprise a portion of a full length antibody, generally the antigen binding or variable domain thereof. Examples of antibody fragments include Fab, Fab', F(ab')$_2$, and Fv fragments; diabodies; linear antibodies; single-chain antibody molecules;

and multispecific antibodies formed from antibody fragments that bind 2 or more different antigens.

The term "immunoconjugates" refers to antibodies or fragment thereof conjugated to another molecule, particularly a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different molecules, e.g., different antigens, or different epitopes on the same molecule).

The term "specificity" refers to the ability to specifically bind (e.g., immunoreact with) a given target. A polypeptide may be monospecific and contain one or more binding sites which specifically bind a target or a polypeptide may be multispecific (e.g., bispecific or trispecific) and contain two or more binding sites which specifically bind the same or different targets.

An antibody of this invention which "binds" or which "recognizes" an antigen or epitope of interest is one that binds the antigen or epitope with sufficient affinity such that the antibody is useful as a diagnostic and/or therapeutic agent in targeting the antigen. With regard to the binding of an antibody, in whole or part, to a target molecule, the term "specific binding" or "specifically binds to" or is "specific to" or is "specifically immunoreactive to" or "specifically recognizes" a particular polypeptide or an epitope on a particular polypeptide target means binding that is measurably different from a non-specific interaction. It includes reference to the preferential association of an antibody, in whole or part, with a cell or tissue bearing the CD52 target molecule and not to cells or tissues lacking that target molecule. Specific binding typically results in greater than two-fold, preferably greater than five-fold, more preferably greater than ten-fold and most preferably greater than one hundred-fold increase in amount of bound ligand to the isolated polypeptide or cell or tissue bearing CD52 as compared to a cell or tissue lacking CD52 or to a non-specific polypeptide. A variety of immunoassay formats are appropriate for selecting antibodies specifically immunoreactive with a particular protein. For example, ELISA immunoassays, FACS assays, Western Blots are routinely used to select monoclonal antibodies specifically immunoreactive with a protein.

An antibody binds "the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. An antibody may be said to competitively inhibit binding of the reference antibody to a given epitope by at least 90%, at least 80%, at least 70%, at least 60%, or at least 50%.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific. For example, the monoclonal antibodies to be used in accordance with the present invention may be made by the hybridoma method first described by Kohler et al., Nature 256:495 (1975), or may be made by recombinant DNA methods. The monoclonal antibodies may also be isolated e.g. from phage antibody libraries.

Monoclonal antibodies are most frequently generated in mice by administration of an "antigen" and subsequent isolation of B-cells that make antibodies. The B-cells are then immortalized by fusion to another, stable cell type of the same species as the B cell to create a "hybridoma". An individual B-cell makes one specific antibody (i.e. is clonally monospecific), which is defined by its primary amino acid sequence and its underlying gene sequence. As used herein, the terms "heterohybridoma" and "heteromyeloma" refer to lymphocyte cell lines immortalized by fusion of lymphocytes and myelomas from two different species.

Monoclonal antibodies can be initially generated, for example, by immunizing animals with an antigen or with cells that express the antigen. The generation of a hybridoma starts with the immunization of mice or companion animals such as dogs. Immunization can be performed with several types of cells in the presence or absence of adjuvants. Cells can also be used to identify the hybridoma cell lines with the desired properties by ELISA, Biacore, FACS or other methodologies available to those in the art.

Cells suitable for use in the methods of monoclonal antibody preparation according to the present invention include: (1) Peripheral Blood Mononuclear Cells (PBMC) or fractions of PBMC enriched in certain type of cells collected from healthy or diseased companion animals such as dogs, cats, or horses. Lymphocytes are pre-incubated in some instances with factors including factors including growth factors such as EPO, SCF, TNFα, TGFβ, GMCSF, TPO, IL-1, IL-2, IL-3, IL-4, GCSF to increase the expression of the antigen prior to immunization. (2) Lymphoma cell lines or tumor cell lines established from healthy or diseased subjects optionally pre-incubated with factors listed above to increase the expression of the antigen prior to immunization. (3) Cell lines derived from tissues of healthy or diseased subjects pre-incubated in some instances with factors listed above to increase the expression of the antigen prior to immunization. (4) Cultured cells engineered to express an antigen coding region or fragment thereof, such as baculovirus-infected cells, bacterial cells, yeast cells, mammalian cells, plant cells, fungal cells and the like. The antigen in the form of DNA, RNA, protein, or peptide, can be included in any one of the fractions of the cell. (5) Magnetic Proteoliposome Particles (MPLs), which are prepared from cells expressing the antigen, such that the native conformation of the transmembrane receptor is maintained, have been described previously (see e.g., Mirzabekov et al. *Nat. Biotechnol.* 18:649-654 (2000); Babcock et al. *J. Biol. Chem.* 276:38433-38440 (2001); PCT Publication WO 01/49265; U.S. Patent Application No. 20010034432).

In certain embodiments of the invention, the generation of monoclonal antibodies can be achieved using immunogens derived from DNA, peptides, or proteins. Hybridomas are generated by immunizing an animal, which can be for example, a mouse or a companion animal, or any animal that will give a suitable antibody response. In one aspect, immunization is performed by introducing into the animal an antigen-encoding nucleic acid, or a protein antigen, such as canine CD52 or an immunogenic fragment thereof, or a nucleic acid encoding CD52 or an immunogenic fragment thereof. The skilled artisan will appreciate that certain epitopes will be more immunogenic in an animal when removed from their native environment. Thus, a peptide corresponding to an epitope of an antigen conjugated to a carrier such as keyhole limpet hemocyanin, may elicit a stronger antibody response than either the peptide alone or the epitope when part of the native protein on which it is found. Such variations and other immunization schemes are known to the skilled artisan are included in the immunization methods of the invention.

The immunogen can be a plasmid carrying a nucleic acid sequence encoding an antigen or a fragment thereof. In other embodiments of the invention, monoclonal antibodies of the invention can be obtained by screening a library of antibody molecules or fragments thereof derived from immunization of animals. Monoclonal antibodies of the invention can also be obtained from libraries of antibodies or antibody-encoding nucleic acids.

As used herein the term "antigen" is understood to be any substance capable of stimulating antibody production. Also, the term "immunogen" is understood to include any substance used to induce an immune response.

The monoclonal antibodies herein may in some embodiments include "chimeric" antibodies in which a portion of the heavy and/or light chain is identical to or homologous with corresponding sequences from antibodies derived from a particular species or belonging to a particular antibody class or subclass, while the remainder of the chain(s) is identical to or homologous with corresponding sequences in antibodies from another species or belonging to another antibody class or subclass, as well as fragments of such antibodies, exhibiting the desired biological activity (See e.g., U.S. Pat. No. 4,816,567; and Morrison et al., *Proc. Natl. Acad. Sci. USA* 81:6851-6855 (1984)).

"Single-chainFv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is short to allow pairing between the two domains on the same chain, the domains are forced to pair with the complementary domains of another chain and create two antigen-binding sites.

In certain aspects the present invention provides methods for adapting antibodies to the species of an intended therapeutic target. Generally, these methods include "mammalization" which is defined as a method for transferring donor antigen-binding information to a less immunogenic mammal antibody acceptor to generate useful therapeutic treatments. More specifically, the invention provides methods for felinization, equinization and caninization of antibodies.

"Caninization" is defined as a method for transferring non-canine antigen-binding information from a donor antibody to a less immunogenic canine antibody acceptor to generate treatments useful as therapeutics in dogs.

"Felinization" is defined as a method for transferring non-feline antigen-binding information from a donor antibody to a less immunogenic feline antibody acceptor to generate treatments useful as therapeutics in cats.

"Equinization" is defined as a method for transferring non-equine antigen-binding information from a donor antibody to a less immunogenic equine antibody acceptor to generate treatments useful as therapeutics in horses.

Caninized forms of non-canine antibodies provided herein are chimeric antibodies that contain minimal sequence derived from non-canine antibodies. For the most part, caninized antibodies are canine antibody sequences ("acceptor" or "recipient" antibody) in which hypervariable region residues of the recipient are replaced by hypervariable region residues from a non-canine species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the canine antibody are replaced by corresponding non-canine FR residues. Furthermore, caninized antibodies may include residues that are not found in the recipient antibody or in the donor antibody. These modifications are made to further refine antibody performance. The caninized antibody may also comprise at least a portion of an immunoglobulin constant region (Fc) of a canine antibody.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared.times.100. Such alignment can be provided using, for instance, the program Basic Local Alignment Search Tool (BLAST) from the National Center for Biotechnology Information NCBI.

In one preferred embodiment, the recombinant polypeptides, or fragments, derivatives, or modifications thereof, are specifically administered into a patient. In another embodiment, the recombinant polypeptide of the invention, or fragments, derivatives, or modifications thereof, are introduced into cells and/or a tissue while under in vitro or ex vivo conditions, prior to the transplantation of the cells and/or a tissue into a mammalian organism for the purpose of treating, preventing, reducing or otherwise lowering disease conditions or symptoms associated or mediated by the disease.

The terms "fragment" and "region" refer to portions of a polypeptide or nucleic acid molecule that contains at least 10%, 20%, 30%, 40%, 50%, 60%, 70%, 80%, 90%, 95%, or more of the entire length of the reference nucleic acid molecule or polypeptide.

The terms "polynucleotide," "nucleic acid," and "nucleic acid molecule," are used interchangeably herein to refer to polymeric forms of nucleotides of any length. The polynucleotides can contain deoxyribonucleotides, ribonucleotides, and/or their analogs. Polynucleotides can have any three-dimensional structure, and can perform any function, known or unknown. The term polynucleotide includes single-stranded, double-stranded, and triple helical molecules, and encompasses nucleic acids containing nucleotide analogs or modified backbone residues or linkages, which can be synthetic, naturally occurring, or non-naturally occurring, and which have similar binding properties as the reference nucleic acid.

"Oligonucleotide" refers generally to polynucleotides that are between 5 and about 100 nucleotides of single- or double-stranded DNA. For the purposes of this disclosure, the lower limit of the size of an oligonucleotide is two, and there is no upper limit to the length of an oligonucleotide. Oligonucleotides are also known as "oligomers" or "oligos" and can be prepared by any method known in the art including isolation from naturally-occurring polynucleotides, enzymatic synthesis and chemical synthesis.

The terms "polypeptide," "peptide" and "protein" are used interchangeably herein to refer to a polymer of amino acid residues of any length. Polypeptides can have any three-dimensional structure, and can perform any function, known or unknown. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ carboxyglutamate, and O-phosphoserine. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "conservatively modified variants" or "conservative variants" or "variants" applies to both amino acid and nucleic acid sequences. With respect to particular nucleic acid sequences, conservatively modified variants refers to those nucleic acids which encode identical or substantially identical amino acid sequences; or for nucleic acids that do not encode an amino acid sequence, to nucleic acids that are substantially identical. As used herein, "substantially identical" means that two amino acid or polynucleotide sequences differ at no more than 10% of the amino acid or nucleotide positions, typically at no more than 5%, often at more than 2%, and most frequently at no more than 1% of the of the amino acid or nucleotide positions.

Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the alternate alanine codons without altering the encoded polypeptide. Such nucleic acid variations are "silent variations," which are one type of conservatively modified variants. Nucleic acid sequences encoding polypeptides described herein also encompass every possible silent variation of the nucleic acid. The skilled artisan will recognize that each amino acid codon in a nucleic acid (except AUG, which is ordinarily the only codon for methionine, and TGG, which is ordinarily the only codon for tryptophan) can be varied at one or more positions to code for the same amino acid. Accordingly, each silent variation of a nucleic acid that encodes a polypeptide is implicit in each described sequence with respect to the expression product.

"Complementarity" as applied to nucleic acids, refers to the ability of the nucleic acid to form hydrogen bond(s) with another polynucleotide sequence by either traditional Watson-Crick or other non-traditional types of base pairing. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, RNA interference, antisense or triple helix inhibition. Determination of binding free energies for nucleic acid molecules is well known in the art. "Percent complementarity" refers to the percentage of contiguous residues in a nucleic acid molecule that can form hydrogen bonds (e.g., Watson-Crick base pairing) with another nucleic acid molecule. "Perfectly complementary" or "100% complementarity" means that all the contiguous nucleotides of a nucleic acid molecule will hydrogen bond with the same number of contiguous residues in a second nucleic acid molecule. "Substantial complementarity" and "substantially complementary" as used herein indicate that two nucleic acids are at least 90% complementary, typically at least 95% complementary, often at least 98% complementary, and most frequently at least 99% complementary over a region of more than about 15 nucleotides and more often more than about 19 nucleotides.

"Homology" is an indication that two nucleotide sequences represent the same gene or a gene product thereof, and typically means that that the nucleotide sequence of two or more nucleic acid molecules are partially, substantially or completely identical. When from the same organism, homologous polynucleotides are representative of the same gene having the same chromosomal location, even though there may be individual differences between the polynucleotide sequences (such as polymorphic variants, alleles and the like). In certain embodiments, a homolog can be found in a non-native position in the genome, e.g. as the result of translocation.

The term "heterologous" refers to any two or more nucleic acid or polypeptide sequences that are not normally found in the same relationship to each other in nature. For instance, a heterologous nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

The term "homolog" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 55%, 57%, 60%, 65%, 68%, 70%, more preferably 80% or 85%, and most preferably 90%, 95%, 98%, or 99% identical at the amino acid level or nucleic acid to a reference sequence.

"Similar" sequences are those which, when aligned, share identical and similar amino acid residues, where similar residues are conservative substitutions for corresponding amino acid residues in an aligned reference sequence. In this regard, conservative residues in a sequence is a residue that is physically or functionally similar to the corresponding reference residue, e.g., that has a similar size, shape, electric charge, chemical properties, including the ability to form covalent or hydrogen bonds, or the like. The "percentage similarity" between two sequences is a function of the number of positions that contain matching residues or conservative residues shared by the two sequences divided by the number of positions compared.times.100.

"Amino acid consensus sequence" as used herein refers to a hypothetical amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids. In some cases, amino acid consensus sequences correspond to a sequence or sub-sequence found in nature. In other cases, amino acid consensus sequences are not found in nature, but represent only theoretical sequences.

The amino acid sequence of a protein can be analyzed at various levels. For example, conservation or variability can be exhibited at the single residue level, multiple residue level, multiple residues with gaps etc. Residues can exhibit conservation of the identical residue or can be conserved at the class level. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Other classes are known to one of skill in the art and may be defined using structural determinations or other data to assess substitutability.

Regarding amino acid sequences, one of skill in the art will recognize that individual substitutions, deletions or insertions to a nucleic acid, peptide, polypeptide, or protein sequence which alters, inserts or deletes a single amino acid or a small percentage of amino acids in the encoded sequence is a "conservatively modified variant" where the alteration results in the substitution of an amino acid with a chemically similar amino acid. Conservative substitution tables detailing functionally similar amino acids are well known in the art. Such conservatively modified variants are in addition to and do not exclude functionally equivalent polymorphic variants, homologs, and alleles of the invention.

As used herein, when one amino acid sequence (e.g., a first VH or VL sequence) is aligned with one or more additional amino acid sequences (e.g., one or more VH or VL sequences in a database), an amino acid position in one sequence (e.g., the first VH or VL sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

As used herein, the term "antibody database" refers to a collection of two or more antibody amino acid sequences (a "plurality" or "multiplicity" of sequences), and typically refers to a collection of tens, hundreds or even thousands of antibody amino acid sequences. An antibody database can store amino acid sequences of, for example, a collection of antibody VH regions, antibody VL regions or both, or can store a collection of framework sequences. In one embodiment, the antibody database is a database comprising or consisting of germline antibody sequences. In another embodiment, the antibody database is a database comprising or consisting of mature antibody sequences (e.g., a Kabat database of mature antibody sequences). In another embodiment, the antibody database comprises or consists of sequences selected for one or more properties. In another embodiment, the antibody database comprises or consists of consensus sequences. In another embodiment, the antibody database comprises or consists of similar sequences. In yet another embodiment, the antibody database comprises or consists of sequences from major antibody clans (Das et al., *Immunogenetics,* 60:47-55 (2008); Das et al., *Proc. Natl. Ac. Sci. USA.* 105:16647-16652 (2008)).

As used herein, the term "property" or "characteristic" is a property of a polypeptide which is desirable and/or advantageous to one of skill in the art, e.g., in order to improve the manufacturing properties or therapeutic efficacy of the polypeptide. In one embodiment, the functional property is improved stability. In another embodiment, the functional property is improved solubility. In yet another embodiment, the functional property is non-aggregation. In still another embodiment, the functional property is an improvement in expression. In certain embodiments, the functional property is an improvement in antigen binding affinity.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transfectants", "transformed cells" and "transfected cells" include the primary subject cell and cultures derived from.

Immunogenic, as used herein, refers to antigens, (including native antigens, fragments, mutant, and derivatives thereof, as well as recombinant and synthetic antigens), that, when introduced into an animal, elicit an immune response, such as a humoral or antibody response.

As used herein, the term "not immunogenic" or "non-immunogenic" means that an antigen, such as an antibody, or other molecule, does not raise an antibody response of sufficient magnitude to reduce the effectiveness of continued administration of the antibody in the majority of treated patients for sufficient time to achieve therapeutic efficacy.

The term "cytokine" refers to all mammalian, preferably from companion animals, cytokines that bind extracellular receptors upon the cell surface and thereby modulate cell function, including but not limited to IL-1, IL-4, IL-6, IL-18, TNF-A, and IFN-gamma. Cytokines are released by cells of the immune system and act as intracellular modulators in the generation of an immune response. Also included in this definition are chemokines. The term "chemokine" refers to all chemotactic cytokines expressed within mammalian organisms that mediate the recruitment and infiltration of leukocytes into tissues. The term "chemokine" includes but is not limited to all mammalian members of the C, CC, CXC, and CXXXC families of chemotactic cytokines, classified based upon the distribution of cysteine residues therein. The term "chemokine receptor" refers to all transmembrane proteins to interact with one or more chemokines.

The term "cytokine receptor" refers to all mammalian, cytokine receptors that bind one or more cytokine(s), including but not limited to receptors of IL-1, IL-4, IL-6, IL-18, TNF-.alpha. The term "chemokine receptor" shall include but is not limited to all chemokine receptors classified as CR, CCR, CXCR and CXXXCR.

As used herein, the term "therapeutic" encompasses the full spectrum of treatments for a "disease" or "disorder" or "condition". A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of a disease or disorder; or may act to minimize the time required, the occurrence or extent of any discomfort or pain, or physical limitations associated with recuperation from a disease, disorder or physical trauma; or may be used as an adjuvant to other therapies and treatments.

"Treatment," as used herein, covers any administration or application of remedies for disease in an animal, including a human, and includes inhibiting the disease, i.e., arresting its development; relieving the disease, i.e., causing its regression; and eliminating the disease, i.e., causing the removal of diseased cells or restoration of a non-diseased state. Treatment refers to both therapeutic treatment and prophylactic or preventative measures. Those in need of treatment include those already with the disorder as well as those in which the disorder is to be prevented.

A "pharmaceutical composition" or "pharmaceutically acceptable composition" of antibodies, polypeptides, or polynucleotides herein refers to a composition that usually contains a pharmaceutically acceptable carrier or excipient that is conventional in the art and which is suitable for administration into a subject for therapeutic, diagnostic, or prophylactic purposes. For example, compositions for oral administration can form solutions, suspensions, tablets, pills, capsules, sustained release formulations, oral rinses, or powders.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a chemotherapeutic agent and an antibody. Alternatively, a combination therapy may involve the administration of an antibody and/or one or more chemotherapeutic agents, alone or together with the delivery of another treatment, such as radiation therapy and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending veterinarian or attending caregiver.

The term "monotherapy" refers to a treatment regimen based on the delivery of one therapeutically effective compound, whether administered as a single dose or several doses over time.

"Immune conditions" are a generic name for a wide range of diseases including arthritis, psoriasis, inflammatory bowel disease, multiple sclerosis, myocardial infarction, stroke, hemolytic anemia, atopic dermatitis, skin disorders, and the like, in which the immune system or a part thereof, such as a cell of the immune system, is abnormal or causes a disease state. Immune conditions include primary defects in an immune cell, tissue or organ, as well as "autoimmune conditions," in which the normal mechanisms for preventing immune recognition of self antigens is defective, resulting in a disease or disorder involving a non-immune cell, tissue or organ type. Cancer such as leukemias and lymphomas are primary immune disorders, while multiple sclerosis and lupus are believed to be of autoimmune origin.

A multitude of therapeutic agents have been developed over the past few decades for the treatment of various types of immune conditions for humans and these have also been used for the treatment of immune conditions in companion animals. The most commonly used types of anti-immune agents include: immunosuppressant agents (e.g., cyclosporine, thiopurine, prednisone), and analgesic and antipyretic (e.g., aspirin, ibuprofen, naproxen, celecoxib, nimesulide, licofelone, omega-3-fatty acids), each of which may be administered simultaneously, sequentially or in a common dosage regimen with antibodies of the invention. (see, for e.g., Withrow & MacEwen's, Small Animal Clinical Oncology, Saunders Elsevier, $4^{th}$ ed. (2007)).

"Cancer" as used herein, refers to any abnormal cell or tissue growth, e.g., a tumor, which can be malignant or non-malignant. Cancer is characterized by uncontrolled proliferation of cells that may or may not invade the surrounding tissue and, hence, may or may not metastasize to new body sites. Cancer encompasses carcinomas, which are cancers of epithelial cells (e.g. squamous cell carcinoma, adenocarcinoma, melanomas, and hepatomas). Cancer also encompasses sarcomas, which are tumors of mesenchymal origin, (e.g. osteogenic sarcomas, leukemias, and lymphomas). Cancers can involve one or more neoplastic cell type. Cancer a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer for humans and have been used off-label or reformulated for the treatment of cancer in companion animals. The most commonly used types of anti-cancer agents include: DNA-alkylating agents (e.g., cyclophosphamide, ifosfamide), anti-metabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and immunosuppressant (e.g., prednisone), each of which may be administered simultaneously, sequentially or in a common dosage regimen with antibodies of the invention.

Antibodies (mAbs) that can be subjected to the techniques set forth herein include monoclonal and polyclonal mAbs, and antibody fragments such as Fab, Fab', F(ab')2, Fd, scFv, diabodies, antibody light chains, antibody heavy chains and/or antibody fragments derived from various sources. An antibody is obtained from a sequence donor species. More particularly, the nucleic acid or amino acid sequence of the variable portion of the light chain, heavy chain or both, of the donor species antibody has specificity for a desired antigen. The donor species is any species which was used to generate the antibodies or antibody libraries, e.g., mouse, rat, rabbit, cat, dogs, goat, chicken, bovine, horse, llama, camel, dromedaries, sharks, non-human primates, human, humanized, recombinant sequence, engineered sequence, etc. Techniques for generating and cloning monoclonal antibodies are well known to those skilled in the art.

After sequencing the antibody obtained from the donor species or from a library, the variable regions (VH and VL) are separated into discrete regions such as leader sequences, frameworks (FRs) and CDRs using any published definition of CDRs and frameworks (e.g., Kabat, Chothia, AbM, contact definition and any combination thereof, and any others known to those skilled in the art). In a particular embodiment, FRs and CDRs are identified with reference to the Kabat definitions.

Whenever it appears herein, a numerical range such as "1 to 100" refers to each integer in the given range; e.g., "1 to 100 nucleotides" means that the nucleic acid can contain only 1 nucleotide, 2 nucleotides, 3 nucleotides, etc., up to and including 100 nucleotides.

With respect to the constant domains of heavy chains, a constant domain or fragment thereof of any subclass from the target species may be fused to the heavy chain heterochimeric variable domains.

The engineering of the recombinant antibody of the claimed invention can be created by introducing modifications, additions or deletions to a nucleic acid encoding the antibody can be introduced by a method comprising recombination, error-prone PCR, shuffling, oligonucleotide-directed mutagenesis, assembly PCR, sexual PCR mutagenesis, in vivo mutagenesis, site-specific mutagenesis, gene reassembly, synthetic ligation reassembly or a combination thereof.

Further envisioned within the scope of this invention is the usage of the recombinant nucleic acids or proteins, or fragments or derivatives thereof, for the treatment of all companion animal diseases and/or conditions that are mediated or associated with the onset of inflammation, as well as companion animal diseases and/or conditions that are mediated or associated with autoimmunity. Such diseases and/or conditions are referred to herein as inflammatory disorders and include but are not restricted to inflammation, autoimmune disease and immune-mediated.

In a further aspect, the invention features pharmaceutical compositions in which antibodies of the present invention are provided for therapeutic or prophylactic uses. The invention features a method for treating a dog subject having a particular antigen, e.g., one associated with disease. The method includes administering a therapeutically effective amount of a recombinant antibody specific for the particular antigen, with the recombinant antibody described herein.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. The route of administration of the antibody or antigen-binding moiety of the invention may be oral, parenteral, by inhalation or topical. The term parenteral as used herein includes intravenous, intramuscular, subcutaneous, rectal, vaginal or intraperitoneal administration.

Antibodies produced in the manner described above, or by equivalent techniques, can be purified by a combination of affinity and size exclusion chromatography for characterization in functional biological assays. These assays include determination of specificity and binding affinity as well as effector function associated with the expressed isotype, e.g., ADCC, apoptosis, or complement fixation. Such antibodies may be used as passive or active therapeutic agents against a number of diseases, including B cell lymphoma, T cell lymphoma, autoimmune diseases, inflammatory diseases, infectious diseases, and transplantation.

"Antibody-dependent cell-mediated cytotoxicity" and "ADCC" refer to a cell-mediated reaction in which nonspecific cytotoxic cells such as Natural Killer (NK) cells, neutrophils, and macrophages recognize bound antibody on a target cell and subsequently cause lysis of the target cell (see, for e.g., Janeway et al., Immuno Biology: Elsevier Science Ltd., 4th ed., (1999)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen.

An "enhanced" or "reduced" ADCC or CDC activity, as used herein, generally refers to a heavy chain that confers more activity or less activity than a reference heavy chain. As would be understood in the art, amount of an activity may be determined quantitatively or qualitatively in parallel or in separate runs according to any assay or technique known in the art.

In certain embodiments of the above aspects, the antigen is a tumor antigen, an antigen involved in an immune disorder, an antigen involved in an autoimmune response, a receptor expressed on a host cell or available in blood circulation or secreted by a cell and the recombinant antibody is able to either deplete undesired cells or to block or stimulates receptor functions, or neutralizes active soluble products.

The antibodies (or fragments thereof) of this invention may also be useful for treating tumors in companion animals. More specifically, they should be useful for reducing tumor size, inhibiting tumor growth and/or prolonging the survival time of tumor-bearing animals. Accordingly, this invention also relates to a method of treating tumors in a dog or other animals by administering an effective dose. An effective dose is expected to be in the range of about 0.05 to 100 milligrams per kilogram body weight per day.

In a particular embodiment, the invention provides antibodies to CD52. The small cell-surface glycoprotein CD52, commonly called the CAMPATH-1 antigen, is a widely distributed membrane-bound protein occurring on a variety of cells including but not limited to lymphocytes, monocytes, thymocytes, epithelial cells, macrophages, peripheral blood cells, dendritic cells, eosinophils, mast cells and several tumor cell lines such as osteogenic tumor cells. In some cases, CD52 or a fragment thereof may be a soluble protein.

A variety of cells expressing the antigen CD52 are associated with diseases such as cancers and immune conditions. Several studies have demonstrated or disclosed that neutralization of human CD52-expressing cells can improve tumor cell or neoplasia either alone or in combination with other anti-cancer or chemotherapeutic agents or treatments.

Myeloid lineage immune cell, containing a number of membrane-bound proteins including CD52, secrete a variety of cytokines and enzymes that result in inflammation. As some of these substances occur in secretory vesicles that appear granular, the process of secretion is sometimes called degranulation. Rapid degranulation by mast cells contributes to the pathology of asthma, anaphylaxis, and other allergic responses, while slower degranulation by mast cells contributes to arthritis and other types of chronic inflammation. The release of inflammatory cytokines and enzymes by mast cells can result in tissue damage, further attraction of mast cells, resulting in further tissue damage.

Macrophages are white blood cells found within tissues produced by the division of monocytes that contain a number of membrane-bound proteins including CD52. These cells are involved in the innate immunity and cell-mediated immunity with a role of phagocytosis of cellular debris and pathogens and to stimulate lymphocytes and other immune cells. Macrophages are involved in many diseases of the immune system. Macrophages are the predominant cells involved in creating the progressive plaque lesions of atherosclerosis. Macrophages are believed to promote proliferation and inflammation of cancerous cells.

Novel and specific treatments targeting proteins on the surface of cells involved in animal diseases may be used to diagnose and treat such diseases with polyclonal antibodies or fragment thereof, monoclonal antibodies or fragment thereof, polypeptides or fragment thereof and other agents which specifically recognize the cell surface targets. In particular, novel antibodies and other agents disclosed herein which specifically recognize targets on the surface of cells that can modulate, (reduce and/or enhance), the disease-promoting activities of cells carrying antigens such CD52. The present invention provides antibodies and polypeptides targeting antigens that are capable of inhibiting the disease-associated activities of cells expressing these antigens either on the membrane or released in blood circulation. In another aspect, the invention provides novel compounds for use in diagnostic assays, and for use as antigens or for selecting antibodies to antigens such CD52.

The invention thus provides: antibodies and/or fragments thereof that include (i) hypervariable region sequences wholly or substantially identical to sequences found in antibodies from a donor species; (ii) constant region sequences wholly or substantially identical to sequences found in antibodies from a target species which is different from the donor species; and (iii) heavy and/or light chain variable framework sequences which contain at least three contiguous non-CDR residues corresponding to sequences found in antibodies from a target species and at least three contiguous non-CDR residues corresponding to sequences found in antibodies from a donor species.

In certain embodiments antibodies of the present invention target antigens associate with a particular disease or disorder, such as acute inflammation, rheumatoid arthritis, transplant rejection, asthma, allergic inflammation, restenosis, arterial restenosis, inflammatory bowel disease, uveitis, multiple sclerosis, psoriasis, wound healing, lupus erythematosus, allergic rhinitis, atopic dermatitis, food allergies, diabetes mellitus, dermatitis, thrombotic thrombocytopenic purpura, encephalitis, leukocyte adhesion deficiency, rheumatic fever, psoriatic arthritis, osteoarthritis, ocular inflammatory disorders, progressive systemic sclerosis, primary biliary cirrhosis, CNS inflammatory disorder, antigen-antibody complex mediated diseases, autoimmune hemolytic anemia, ischemic heart disease, atherosclerosis, post-dialysis syndrome, leukemia, acquired immune deficiency syndrome, septic shock, lipid histiocytosis, and cancer.

Of particular interest is antigen CD52. The skilled artisan will appreciate that the antigen is preferably isolated or derived from the target species (e.g. canine, feline or equine), but suitable cross-reactive antibodies can in some cases be generated by using an antigen from a xenogenic species.

1.1. The antibody of any of the previous embodiments wherein the complementarity determining regions and framework regions are defined in accordance with Kabat.

1.2. The antibody of any of the previous embodiments wherein the constant region of the antibody is modified to enhance a cytotoxic effector functions selected from ADCC, antibody dependent cellular phagocytosis (ADCP), and complement dependent cytotoxicity (CDC).

In a further embodiment, the invention provides

2. Antibody 2, which is an antibody to CD52.

2.1. Antibody 2 wherein the antibody recognizes canine or feline or equine CD52.

2.2. Antibody 2 wherein the antibody is derived from or has substantially the same hypervariable domain as an antibody raised against an immunogenic construct comprising or expressing a peptide containing the sequence of one or more extracellular loops of CD52.

2.3. Any of Antibodies 2 wherein the antibody induces apoptosis of cells expressing CD52.

2.4. Any of Antibodies 2.wherein the antibody suppresses growth of cells expressing CD52.

2.5. Any of Antibodies 2 wherein the antibody causes the death of cells expressing CD52 by antibody dependent cell-mediated cytotoxicity (ADCC).

2.6. Any of Antibodies 2 wherein the antibody causes the death of cells expressing CD52 by complement-dependent cytotoxicity (CDC).

2.7. Any of Antibodies 2 wherein the antibody recognizes feline CD52.

2.8. Any of Antibodies 2 wherein the antibody recognizes canine CD52.

2.9. Antibody 2 wherein the antibody is derived from or has substantially the same hypervariable domain as an antibody raised against an immunogenic construct comprising or expressing a peptide containing a sequence selected from one or more of the sequences of residues 4-18, 20-26, 30-39, 36-47, and/or 49-64 of SEQ ID NO:1.

2.10. Antibody 2 wherein the antibody specifically recognizes an epitope on the extracellular loop of canine CD52, wherein the epitope comprises or is found within a region of the CD52 selected from residues 4-18, 20-26, 30-39, 36-47, and/or 49-64 of SEQ ID NO:1.

2.11. Any of Antibodies 2 wherein the antibody recognizes equine CD52.

2.12. Any of Antibodies 2 wherein the antibody comprises hypervariable sequences from a donor species antibody and constant region sequences from a target species.

2.13. Any of Antibodies 2 wherein the antibody is caninized.

2.14. Any of Antibodies 2 wherein the antibody is felinized.

2.15. Any of Antibodies 2 wherein the antibody is equinized.

2.16. Any of Antibodies 2 wherein the antibody is a heterochimeric antibody of any of Antibodies 1.

2.17. Any of Antibodies 2 wherein the antibody is monoclonal and is fully canine.

2.18. Any of Antibodies 2 wherein the antibody is monoclonal and is fully feline.

2.19. Any of Antibodies 2 wherein the antibody is monoclonal and is fully equine.

The invention further provides a. a method of treating a patient suffering from a disease or condition characterized by the presence of abnormal cells expressing a target antigen comprising administering a therapeutically effective amount of an antibody binding to such target antigen, wherein the antibody is selected from Antibody 1 or 2.

b. a method of treating a patient suffering from a disease or condition characterized by the presence of abnormal cells expressing CD52 comprising administering a therapeutically effective amount of an antibody selected from Antibody 2.

c. Method b) wherein the patient is a dog.

d. Method c) wherein the condition to be treated is an inflammatory disorder.

e. Method a) wherein the disease is selected from the group consisting of: acute inflammation, rheumatoid arthritis, transplant rejection, asthma, allergic inflammation, restenosis, arterial restenosis, inflammatory bowel disease, uveitis, multiple sclerosis, psoriasis, wound healing, lupus erythematosus, allergic rhinitis, atopic dermatitis, food allergies, diabetes mellitus, dermatitis, thrombotic thrombocytopenic purpura, encephalitis, leukocyte adhesion deficiency, rheumatic fever, psoriatic arthritis, osteoarthritis, ocular inflammatory disorders, progressive systemic sclerosis, primary biliary cirrhosis, CNS inflammatory disorder, antigen-antibody complex mediated diseases, autoimmune hemolytic anemia, ischemic heart disease, atherosclerosis, post-dialysis syndrome, leukemia, acquired immune deficiency syndrome, septic shock, lipid histiocytosis, and cancer.

f. Method a, b, c or d or e further comprising administration of chemotherapy.

g. Method f wherein the chemotherapy comprises administration of one or more agents selected from cyclophosphamide, doxorubicin, vincristine, prednisone, L-asparaginase, cytoxan and adriamycin.

h. Method for g wherein the chemotherapy spares or enhances effector cells, e.g., so as to enhance or reduce interference with ADCC effects of antibody on cancer cells.

i. Any of the foregoing methods further comprising administration of a corticosteroid, e.g., prednisone.

j. Any of the foregoing methods further comprising administration of radiation.

k. Any of the foregoing methods comprising co-administration of antibody to CD20 and CD52.

l. Any of the foregoing methods wherein the antibody is administered in a method to treat or inhibit recurrence of cancer following treatment with radiation or chemotherapy.

The invention further provides pharmaceutical compositions comprising any of antibodies 1 or 2, e.g., for use in any of methods a-l.

The invention further provides the use of any of antibodies 1 or 2 as pharmaceuticals, or in the manufacture of a medicament for use in any of the methods a-o.

The invention further provides a cell line stably expressing any of antibodies 1-1 or 2, for example a CHO cell line or a PerC6 stably expressing any of antibodies 1 or 2.

The invention further provides a vector or vectors expressing at least one heavy chain and at least one light chain of any of antibodies 1 or 2.

The invention further provides a method of making an antibody comprising transforming a cell line with a vector or vectors expressing at least one heavy chain and at least one light chain of any of antibodies 1 or 2.

In another embodiment the invention provides a method of diagnosing a disease or condition treatable with the antibodies of the invention, comprising obtaining a tissue sample and measuring binding by one of the antibodies of the invention, together with diagnostic kits for performing such a method comprising an antibody of the invention, e.g., any of antibodies 1 or 2.

Thus the invention provides the following antibodies, as well as functional fragments and conservative variants thereof:

| SEQ ID NO. | Designation |
| --- | --- |
| SEQ ID NO: 5 | VET306 VH-CH (Caninized Mab) |
| SEQ ID NO: 6 | VET306 VL-CL (Caninized Mab) |
| SEQ ID NO: 7 | |
| SEQ ID NO: 8 | VET158 VL-CL (Felinized Mab) |

Other features and advantages of the invention are apparent from the following description of the preferred embodiments thereof, and from the claims.

Example 1

Cloning of CD52

I. Cloning of the Canine CD52 Coding Sequence

CD52 are isolated from canine peripheral blood mononuclear cells (PBMC). Total RNA is extracted from 1 million canine PBMC using the MasterPure™ RNA Purification Kit (Epicentre Biotechnology). The first-strand cDNA is synthesized from 2 μg of total RNA using SuperScript, First-Strand Synthesis, System for RT-PCR kit (Invitrogen) according to the manufacturer's instructions. The coding region or fragment thereof is then amplified by PCR using the primers of SEQ ID NO: 3 and SEQ ID NO: 4. The samples are denatured at 94° C. for 5 min followed by amplifications for 35 cycles (94° C. for 30 s, 62° C. for 20 s, 72° C. for 45 s). The PCR products are cloned into pcDNA3 (Invitrogen) and sequenced.

The amino-acid sequence of the canine CD52 isolated from canine PBMC is reported as SEQ ID No:1

II. Cloning of the Feline CD52 Coding Sequence

The feline CD52 gene is cloned as described above with primers designed to amplify the canine CD52 sequence.

The amino-acid sequence of the feline CD52 isolated from feline PBMC is reported as SEQ ID NO:2

Example 2

Immunization with CD52 and Generation of Murine Monoclonal Antibodies to Canine CD52

Antibodies to CD52 are raised using polypeptides encompassing CD52 amino acid sequences or fragment thereof and/or using cells expressing CD52 gene or a fragment thereof and/or polypeptides isolated from cells expressing CD52 amino acid sequences or fragment thereof. Antibodies are then selected and engineered for use in companion animals.

To generate monoclonal antibodies to canine CD52, CHO-DG44 (Chinese hamster ovary cells, dihydrofolate reductase deficient, ATCC CRL-9096), HEK293 (Human embryonal kidney cells, ATCC CRC-1573) and NIH:3T3 (ATCC CRL-1658) are transfected with an expression vector encoding CD52 as a full length or a fragment thereof. In brief, recombinant canine CD52 that contained an epitope tag are isolated from a transfected CD52-expressing cell line using the detergent CHAPSO and the protein is captured on magnetic beads via the epitope tag.

Anti-CD52 monoclonal antibodies are generated by immunization of mice to raise immunoglobulins specific for canine CD52. Washed cells expressing canine CD52 ($1 \times 10^7$ cells in 100 μL) or 100 μL of CD52 beads ($1 \times 10^9$ beads/ml)

are used as immunogens. Mice are immunized with antigen in Ribi adjuvant intraperitonealy three times, then boosted twice on consecutive days. The immune response is monitored by retro-orbital bleeds. The sera are screened by FACS staining of CD52-expressing cells.

Spleen is harvested from mice with sufficient titers of anti-CD52 immunoglobulin. A murine antibody library is prepared from spleen cells of the mice and displayed on phage such that the phage is then screened for expression of antibodies with specificity for CD52. This combination approach is generally described in U.S. Pat. No. 6,092,098 the contents of which are incorporated herein by reference.

The phage display library is screened for library members having affinity for CD52 by panning with canine CD52 captured onto magnetic beads. Three rounds of panning of the phage display library on the CD52-beads leads to several fold enrichment of CD52-binders as compared to background. Variable region fragments of interest are recloned into a Fab expression vector and the Fab retested for antigen binding against transfected CD52 expressing cells.

Anti-CD52 antibodies with high affinity for the canine CD52 exhibiting efficacy are identified by testing them in a panel of assays using methodologies available to those in the art.

The specific binding of the newly generated anti-CD52 antibodies are assessed by FACS with cells expressing CD52. For cell-binding assay, CD52 expressing cells or canine lymphoma cells are washed with phosphate-buffered saline (PBS) and seeded in wells. After one hour at room temperature to allow cell attachment to the plate surface, the cells are washed with FBS to block non-specific binding sites on the plates. Supernatants from cells expressing the anti-canine CD52 antibodies are then added. After one hour incubation at room temperature, the plates are washed with PBS. The secondary antibody is then added and detected using standard procedures.

Example 3

Heterochimeric Antibodies

The following EXAMPLE provides general representations of heterochimeric antibodies, which are constructed according to standard techniques using the sequences and general patterns illustrated below. In the examples listed below, the CDRs are defined using the Kabat nomenclature.

I. Antibody Variable Domains

Illustrated in Table 1, are diagrammatic representations of the heterochimerization for the light chain (AVD1 to AVD10) and heavy chain (AVD11 to AVD13) antibodies, showing contiguous sequences of discrete immunoglobulin domains. Additional antibody variants are constructed by flanking the variable regions from the donor species with any of the constant domains from the target species.

TABLE 1

| | |
|---|---|
| AVD 1: | FR1-CDR1-FR2-CDR2-FR3-CDR3-FR4$_{T-Lambda}$-C$_{T-Lambda}$ |
| AVD 2: | FR1-CDR1-FR2-CDR2-FR3-CDR3-FR4$_{T-Kappa}$-C$_{T-Lambda}$ |
| AVD 3: | FR1-CDR1-FR2-CDR2-FR3-CDR3-FR4$_{T-Lambda}$-C$_{T-Kappa}$ |
| AVD 4: | FR1-CDR1-FR2-CDR2-FR3-CDR3-FR4$_{T-kappa}$-C$_{T-Kappa}$ |
| AVD 5: | FR1$_{T-Lambda}$-CDR1-FR2-CDR2-FR3-CDR3-FR4$_{T-Lambda}$-C$_{T-Lambda}$ |
| AVD 6: | FR1$_{T-Kappa}$-CDR1-FR2-CDR2-FR3-CDR3-FR4-C$_{T-Lambda}$ |
| AVD 7: | FR1$_{T-Lambda}$-CDR1-FR2-CDR2-FR3-CDR3-FR4-C$_{T-Kappa}$ |
| AVD 8: | FR1$_{T-kappa}$-CDR1-FR2-CDR2-FR3-CDR3-FR4-C$_{T-Kappa}$ |

TABLE 1-continued

| | |
|---|---|
| AVD 9: | FR1$_{T-Lamda}$-CDR1-FR2-CDR2-FR3-CDR3-FR4$_{T-Lambda}$-C$_{T-Lambda}$ |
| AVD 10: | FR1$_{T-kappa}$-CDR1-FR2-CDR2-FR3-CDR3-FR4$_{T-kappa}$-C$_{T-Kappa}$ |
| AVD 11: | FR1-CDR1-FR2-CDR2-FR3-CDR3-FR4$_T$-C$_T$ |
| AVD 12: | FR1$_T$-CDR1-FR2-CDR2-FR3-CDR3-FR4-C$_T$ |
| AVD 13: | FR1$_T$-CDR1-FR2-CDR2-FR3-CDR3-FR4$_T$-C$_T$ |

AVD = Antibody Variable Domain;
T = Target species;
Lambda = lambda light chain;
Kappa = kappa light chain;
C = Constant domain;
FR = Framework region;
CDR = Complementarity Determining Region.

II. Framework Sequences

Exemplary framework sequences used as a source to construct the light chain and heavy chain heterochimeric antibodies are generally described in the U.S. Ser. No. 12/584,390 and PCT/US2009/04997 which applications are incorporated herein by reference.

III. Constant Domain Sequences

Exemplary constant domain sequences used as a source to construct the antibody variants and/or fragments thereof are generally described in the international publication WO 2010/110838, the contents of which are incorporated herein by reference.

Example 4

Testing of the Anti-CD52 Monoclonal Antibody in Dogs

I. Engineering of the Anti-CD52 Monoclonal Antibody

The anti-CD52 monoclonal antibody, designated VET 306, are engineered according to Example 3 using the rat anti-human CD52 antibody with sequences described in pdb 1bfo_E and pdb 1bfo_F (Campath-1G, clone YTH 34.5HL, Protein Data Bank proteins (pdb), date of deposition: May 20, 1998). Variable regions are prepared by assembling synthetic oligonucleotides corresponding to the publically available sequence, and cloned into pSMART with HindIII and NheI as flanking restriction sites on the 5'- and 3'-end of the variable domains, respectively. Assembled products are then subcloned into an expression vector containing a promoter and the heavy chain constant domain or containing the lambda light chain constant domain. The entire expression cassette includes the human cytomegalovirus immediate-early (CMV) promoter, a kozak sequence and signal peptide sequence immediately upstream of the coding sequence and in frame with the variable region of both the light and heavy chains to direct the resulting antibody product towards the secretory pathway.

II. Creation of Anti-CD52 Producing Cell Line and Antibody Production

The vector harboring both the light chain gene and the heavy chain gene of the caninized anti-CD52 antibody (VET 306) is introduced into mammalian cells (PER.C6) to create a cell line expressing the corresponding recombinant antibody at large scale. Cells are cultured in a chemically-defined, protein-free medium CDM4PerMab (Hyclone, Thermo-Scientific, Cat No. SH30871.02) supplemented with 3.0 mM Glutamine (Invitrogen, Gibco, Cat No. 25030-081). Four passages after thaw, the PER.C6 cells are transfected by electroporation with the linearized vector DNA using standard techniques. Cells which stably incorporate the vector are selected for by survival in presence of 125.0 ug/mL Geneticin (Invitrogen, Cat No. 11811-023). Single clones recovered from transfection are further evaluated in large scale culture for antibody titer, binding to CD52-expressing cells, cell doubling time, cell viability, and cell stability and are cryo-frozen following standard techniques. Antibody production and purification are subsequently performed using one clone following standard techniques.

III. Half-life of the Recombinant Anti-CD52

The half-life of the recombinant anti-CD52 antibody (VET 306) is assessed by dosing beagle dogs intravenously. Blood samples are collected for analysis of the antibody in plasma samples harvested as whole blood treated with Ethylenediaminetetraacetic acid (EDTA) as the anticoagulant. An enzyme linked immunosorbant assay (ELISA) method is utilized to determine the plasma antibody concentrations. In this assay, a 96-well plate is coated with a rabbit polyclonal antibody raised to the variable domain of the recombinant anti-CD52. The recombinant anti-CD52 in standards or in samples is captured by the polyclonal antibodies and is detected by an enzyme conjugated anti-dog secondary antibody. A non-linear regression fit of the standards is used to determine the recombinant antibody concentrations in plasma.

Pharmacokinetics studies show that the caninized anti-CD52 antibody achieves high level of plasma in all animals. Half-life ranges between 50.0 to 96.0 hours after the first 10.0 mg dose and 75.0 to 120.0 hours after the first 30.0 mg dose.

Interestingly, the half-life values of the recombinant anti-canine CD52 antibody increase after consecutive administration. Systemic clearance decreases with repeated administration due to decreased receptor-mediated clearance (i.e., loss of CD52 receptors in the periphery).

IV. Depletion of Leukocytes in Vivo

Three beagle dogs receive three consecutive dosages of the recombinant anti-CD52 antibody ranging from 0.05 mg/kg to 3.0 mg/kg every 3 days. Blood samples are drawn at several time points. Blood samples are centrifuged at 2000 RPM for 5 min. Plasma is removed for assay of the recombinant antibody levels. The pellet (containing peripheral blood leukocytes and red blood cells) is resuspended in a plasma equivalent volume of phosphate saline solution (Dulbecco's Phosphate-Buffered Saline, Mediatech, Cat No. 21-030-CM) for quantitation of leukocyte populations by flow cytometry. A 0.1 mL volume of the cell preparation is distributed into micro-centrifuge tubes. A labeled monoclonal antibody with specificity for the canine leukocyte surface marker CD45 (Rat anti-dog CD45:Alexa Flor 488, AbDSerotec, Cat No. MCS1042A488) is added to the vial to identify the leukocyte cell population. An additional sample is included with no reagents for determination of autofluorescence. Cells are incubated with the fluorescent antibody for 30 min. Red blood cell are then lyzed for 15 min using a lysis buffer (Red Blood Cell Lysis Buffer, Biolegend, Cat No. 420301) and subsequently washed prior to analysis on a Becton Dickinson FACS instrument.

Interestingly, a dose of 1.0 mg/kg of the recombinant anti-CD52 antibody triggers leukocyte depletion ranging from 36 to 95% of the pre-dosing level.

Dosing of the recombinant anti-CD52 antibody over a period of 21 days is well tolerated locally and systemically and no adverse effects are noticed on clinical and behavioral observations or body weights.

Example 5

Treatment with Anti-CD52 Antibody

I. Treatment of Dogs

A dog diagnosed with an immune condition including lymphoma, relapsed lymphoma, leukemia, mast cell tumor, hemolytic anemia, arthritis, atopic dermatitis is given therapy with the anti-CD52 monoclonal antibody. The dog is infused intravenously or subcutaneously with 1-5 mg/kg of antibody, and the treatment is repeated weekly for 4-8 weeks following the initial treatment. Two months after the final dose, the patient shows reduced levels of certain types of cells expressing CD52. The dog is then treated under a maintenance regimen with administration of the anti-CD52 antibody every 8-12 weeks.

II. Treatment of Atopic Dermatitis

Dogs with confirmed atopic dermatitis receive 1 mg/kg of treatment two to three times a week for an initial four weeks. Clinical response to treatment is assessed (i) for dermatologic lesions using a Canine Atopic Dermatitis Extent Severity Index (CADESI), and (ii) for pruritus after the initial four weeks of treatment. After the pruritus scores and CADESI scores showed improvement, the dose and frequency of the administration is decreased. Two months after the final dose, the patient shows overall improvement.

III. Treatment of Cats

A cat diagnosed with an immune condition including lymphoma, relapsed lymphoma, leukemia, mast cell tumor, hemolytic anemia, arthritis, atopic dermatitis is given therapy with the anti-CD52 monoclonal antibody. The cat is infused intravenously or subcutaneously with 5 mg/kg of antibody, and the treatment is repeated weekly for 4-8 weeks following the initial treatment. Two months after the final dose, the patient shows reduced levels of certain types of cells expressing CD52.

IV. Treatment of Horses

A horse diagnosed with an immune condition including lymphoma, relapsed lymphoma, leukemia, mast cell tumor, hemolytic anemia, arthritis, atopic dermatitis is given therapy with the anti-CD52 monoclonal antibody. The horse is infused intravenously or subcutaneously with 5 mg/kg of antibody, and the treatment is repeated weekly for 4-8 weeks following the initial treatment. Two months after the final dose, the patient shows reduced levels of certain types of cells expressing CD52.

Alternative combinations and variations of the examples provided will become apparent based on this disclosure. It is not possible to provide specific examples for all of the many possible combinations and variations of the embodiments described, but such combinations and variations are nevertheless intended to be within the scope of the invention.

SEQUENCE LISTING

| SEQ ID NO. | Designation | Sequence |
|---|---|---|
| SEQ ID NO: 1 | VET 405 Canine CD52 | MKGFLFLLLTISLLVMIQIQTGVLGNSTTPRMTTKKVKSATPALSS LGGGSVLLFLANTLIQLFYLS |
| SEQ ID NO: 2 | Vet 420 Feline CD52 | MKGFLFLLLTISLLVMIQIQTGVLGNTTTAATTTKKPKSATPPLSS LSSGSVLLFLANILVQLFYLS |
| SEQ ID NO: 3 | CD52 F | 5'-CAACAAAGCTTGCCGCCACCATGAAGGGCTTCCTCTTCCT-3' |
| SEQ ID NO: 4 | CD52 R | 5'-CAACAGGATCCTCAGCTGAGGTAGAAGAGCT-3' |
| SEQ ID NO: 5 | VET306 VH-CH (Caninized Mab) | EVKLLESGGGLVQPGGSMRLSCAGSGFTFTDFYMNWIRQPAGKAP EWLGFIRDKAKGYTTEYNPSVKGRFTISRDNTQNMLYLQMNTLRA EDTATYYCAREGHTAAPFDYWGQGTLVTVSSASTTAPSVFPLAPS CGSTSGSTVALACLVSGYFPEPVTVSWNSGSLTSGVHTFPSVLQS SGLYSLSSMVTVPSSRWPSETFTCNVAHPASKTKVDKPVPKRENG RVPRPPDCPKCPAPEMLGGPSVFIFPPKPKDTLLIARTPEVTCVV VDLDPEDPEVQISWFVDGKQMQTAKTQPREEQFNGTYRVVSVLPI GHQDWLKGKQFTCKVNNKALPSPIERTISKARGQAHQPSVYVLPP SREELSKNTVSLTCLIKDFFPPDIDVEWQSNGQQEPESKYRTTPP QLDEDGSYFLYSKLSVDKSRWQRGDTFICAVMHEALHNHYTQKSL SHSPGK |
| SEQ ID NO: 6 | VET306 VL-CL (Caninized Mab) | DIKMTQSPSFLSASVGDRVTLNCKASQNIDKYLNWYQQKLGESPK LLIYNTNNLQTGIPSRFSGSGSGTDFTLTISSLQPEDVATYFCLQ HISRPRTFGGGTHLTVLGQPKASPSVTLFPPSSEELGANKATLVC LISDFYPSGVTVAWKADGSPITQGVETTKPSKQSNNKYAASSYLS LTPDKWKSHSSFSCLVTHEGSTVEKKVAPAECS |
| SEQ ID NO: 7 | VET279 VH-CH (Felinized Mab) | EVKLLESGGGLVQPGGSMRLSCAGSGFTFTDFYMNWIRQPAGKAP EWLGFIRDKAKGYTTEYNPSVKGRFTISRDNTQNMLYLQMNTLRA EDTATYYCAREGHTAAPFDYWGQGTLVTVSSASTTAPSVFPLAPS CGTTSGATVALACLVLGYFPEPVTVSWNSGALTSGVHTFPSVLQA SGLYSLSSMVTVPSSRWLSDTFTCNVAHPPSNTKVDKTVRKTDHP PGPKPCDCPKCPPPEMLGGPSIFIFPPKPKDTLSISRTPEVTCLV VDLGPDDSDVQITWFVDNTQVYTAKTSPREEQFNSTYRVVSVLPI LHQDWLKGKEFKCKVNSKSLPSPIERTISKDKGQPHEPQVYVLPP AQEELSRNKVSVTCLIEGFYPSDIAVEWEITGQPEPENNYRTTPP OLDSDGTYFLYSRLSVDRSWQRGNTYTCSVSHEALHSHHTQKSL THSPGK |
| SEQ ID NO: 8 | VET158 VL-CL (Felinized Mab) | DIKMTQSPSFLSASVGDRVTLNCKASQNIDKYLNWYQQKLGESPK LLIYNTNNLQTGIPSRFSGSGSGTDFTLTISSLQPEDVATYFCLQ HISRPRTFGTGTKLEIKRSDAQPSVFLFQPSLDELHTGSASIVCI LNDFYPKEVNVKWKVDGVVQNKGIQESTTEQNSKDSTYSLSSTLT MSSTEYQSHEKFSCEVTHKSLASTLVKSFNRSECQRE |

---

The invention claimed is:

1. An antibody or antibody fragment recognizing a canine or feline CD52, and comprising a variable domain, wherein the variable domain comprises six CDR regions wherein the CDR regions are independently selected from the CDRs in a sequence selected from SEQ ID NOS: 5-8, wherein the CDR regions are as defined by Kabat, and wherein the antibody or antibody fragment comprises a light chain and a heavy chain and wherein the antibody or antibody fragment further comprises a constant domain which comprises sequences of canine or feline origin.

2. An antibody or antibody fragment according to claim 1 recognizing canine or feline CD52, wherein said variable domain comprises a variable domain from a sequence selected from SEQ ID NOS: 5-8.

3. An antibody or antibody fragment according to claim 1 comprising a variable domain structure selected from AVD-1 through AVD-13.

4. The antibody or antibody fragment according to claim 1 which is a heterochimeric antibody.

5. The antibody or antibody fragment according to claim 1 which binds to canine CD52 and wherein the constant region is of canine origin.

6. The antibody or antibody fragment according to claim 1 which binds to feline CD52 and wherein the constant region is of feline origin.

7. The antibody or antibody fragment according to claim 1 wherein the constant domain comprises a sequence selected for providing enhanced ADCC and/or CDC.

8. A method of treating an animal suffering from a disease or condition characterized by overproliferation of cells expressing CD52 comprising administering an effective amount of an antibody of antibody fragment according to claim 1.

9. The method of claim 8 wherein the disease or condition is a cancer.

10. The method of claim 8 wherein the disease or condition is an inflammatory disease.

11. The method of claim 8 comprising co-administration of a chemotherapeutic drug, or a second monoclonal antibody.

12. The method of claim 8 wherein the animal is diagnosed as suffering from a disease or condition characterized by overproliferation of cells expressing CD52 using a diagnostic assay comprising an antibody to CD52.

13. The antibody or antibody fragment of claim 1, wherein the antibody or antibody fragment is an antibody which recognizes a canine CD52, wherein the constant region is of canine origin, and wherein the antibody or antibody fragment comprises SEQ ID NO: 5.

14. The antibody or antibody fragment of claim 1, wherein the antibody or antibody fragment is an antibody which recognizes a canine CD52, wherein the constant region is of canine origin, and wherein the antibody or antibody fragment comprises SEQ ID NO: 6.

15. The antibody or antibody fragment of claim 1, wherein the antibody or antibody fragment recognizes a feline CD52, wherein the constant region is of feline origin, and wherein the antibody or antibody fragment comprises SEQ ID NO: 7.

16. A cell line stably expressing the antibody of claim 1.

17. The antibody or antibody fragment of claim 1, wherein the antibody or antibody fragment recognizes a feline CD52, wherein the constant region is of feline origin, and wherein the antibody or antibody fragment comprises SEQ ID NO: 8.

18. The antibody or antibody fragment of claim 1, wherein the antibody or antibody fragment is an antibody which recognizes canine CD52, the antibody comprising a heavy chain comprising SEQ ID NO: 5 and a light chain comprising SEQ ID NO: 6.

19. The antibody or antibody fragment of claim 1, wherein the antibody or antibody fragment is an antibody which recognizes feline CD52, the antibody comprising a heavy chain comprising SEQ ID NO: 7 and a light chain comprising SEQ ID NO: 8.

* * * * *

SEQUENCE LISTING

<160> NUMBER OF SEQ ID NOS: 8

<210> SEQ ID NO 1
<211> LENGTH: 67
<212> TYPE: PRT
<213> ORGANISM: Canis

<400> SEQUENCE: 1

Met Lys Gly Phe Leu Phe Leu Leu Thr Ile Ser Leu Leu Val Met
1               5                   10                  15

Ile Gln Ile Gln Thr Gly Val Leu Gly Asn Ser Thr Thr Pro Arg Met
            20                  25                  30

Thr Thr Lys Lys Val Lys Ser Ala Thr Pro Ala Leu Ser Ser Leu Gly
        35                  40                  45

Gly Gly Ser Val Leu Leu Phe Leu Ala Asn Thr Leu Ile Gln Leu Phe
    50                  55                  60

Tyr Leu Ser

-continued

65

<210> SEQ ID NO 2
<211> LENGTH: 67
<212> TYPE: PRT
<213> ORGANISM: Felis

<400> SEQUENCE: 2

Met Lys Gly Phe Leu Phe Leu Leu Thr Ile Ser Leu Leu Val Met
1               5                   10                  15

Ile Gln Ile Gln Thr Gly Val Leu Gly Asn Thr Thr Ala Ala Thr
                20                  25                  30

Thr Thr Lys Lys Pro Lys Ser Ala Thr Pro Pro Leu Ser Ser Leu Ser
            35                  40                  45

Ser Gly Ser Val Leu Leu Phe Leu Ala Asn Ile Leu Val Gln Leu Phe
    50                  55                  60

Tyr Leu Ser
65

<210> SEQ ID NO 3
<211> LENGTH: 40
<212> TYPE: DNA
<213> ORGANISM: Canis

<400> SEQUENCE: 3
caacaaagct tgccgccacc atgaagggct tcctcttcct                          40

<210> SEQ ID NO 4
<211> LENGTH: 31
<212> TYPE: DNA
<213> ORGANISM: Artificial Sequence
<220> FEATURE:
<223> OTHER INFORMATION: CD52 F

<400> SEQUENCE: 4
caacaggatc ctcagctgag gtagaagagc t                                   31

<210> SEQ ID NO 5
<211> LENGTH: 456
<212> TYPE: PRT
<213> ORGANISM: Artificial Sequence
<220> FEATURE:
<223> OTHER INFORMATION: VET306 VH-CH

<400> SEQUENCE: 5

Glu Val Lys Leu Leu Glu Ser Gly Gly Gly Leu Val Gln Pro Gly Gly
1               5                   10                  15

Ser Met Arg Leu Ser Cys Ala Gly Ser Gly Phe Thr Phe Thr Asp Phe
                20                  25                  30

Tyr Met Asn Trp Ile Arg Gln Pro Ala Gly Lys Ala Pro Glu Trp Leu
            35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser Ala Ser Thr Thr Ala Pro Ser
        115                 120                 125

```
Val Phe Pro Leu Ala Pro Ser Cys Gly Ser Thr Ser Gly Ser Thr Val
    130                 135                 140

Ala Leu Ala Cys Leu Val Ser Gly Tyr Phe Pro Glu Pro Val Thr Val
145                 150                 155                 160

Ser Trp Asn Ser Gly Ser Leu Thr Ser Gly Val His Thr Phe Pro Ser
                165                 170                 175

Val Leu Gln Ser Ser Gly Leu Tyr Ser Leu Ser Ser Met Val Thr Val
            180                 185                 190

Pro Ser Ser Arg Trp Pro Ser Glu Thr Phe Thr Cys Asn Val Ala His
            195                 200                 205

Pro Ala Ser Lys Thr Lys Val Asp Lys Pro Val Pro Lys Arg Glu Asn
    210                 215                 220

Gly Arg Val Pro Arg Pro Pro Asp Cys Pro Lys Cys Pro Ala Pro Glu
225                 230                 235                 240

Met Leu Gly Gly Pro Ser Val Phe Ile Phe Pro Pro Lys Pro Lys Asp
                245                 250                 255

Thr Leu Leu Ile Ala Arg Thr Pro Glu Val Thr Cys Val Val Val Asp
            260                 265                 270

Leu Asp Pro Glu Asp Pro Glu Val Gln Ile Ser Trp Phe Val Asp Gly
            275                 280                 285

Lys Gln Met Gln Thr Ala Lys Thr Gln Pro Arg Glu Glu Gln Phe Asn
    290                 295                 300

Gly Thr Tyr Arg Val Val Ser Val Leu Pro Ile Gly His Gln Asp Trp
305                 310                 315                 320

Leu Lys Gly Lys Gln Phe Thr Cys Lys Val Asn Asn Lys Ala Leu Pro
                325                 330                 335

Ser Pro Ile Glu Arg Thr Ile Ser Lys Ala Arg Gly Gln Ala His Gln
            340                 345                 350

Pro Ser Val Tyr Val Leu Pro Pro Ser Arg Glu Glu Leu Ser Lys Asn
            355                 360                 365

Thr Val Ser Leu Thr Cys Leu Ile Lys Asp Phe Phe Pro Pro Asp Ile
    370                 375                 380

Asp Val Glu Trp Gln Ser Asn Gly Gln Gln Glu Pro Glu Ser Lys Tyr
385                 390                 395                 400

Arg Thr Thr Pro Pro Gln Leu Asp Glu Asp Gly Ser Tyr Phe Leu Tyr
                405                 410                 415

Ser Lys Leu Ser Val Asp Lys Ser Arg Trp Gln Arg Gly Asp Thr Phe
            420                 425                 430

Ile Cys Ala Val Met His Glu Ala Leu His Asn His Tyr Thr Gln Lys
            435                 440                 445

Ser Leu Ser His Ser Pro Gly Lys
    450                 455

<210> SEQ ID NO 6
<211> LENGTH: 213
<212> TYPE: PRT
<213> ORGANISM: Artificial Sequence
<220> FEATURE:
<223> OTHER INFORMATION: VET306 VL-CL

<400> SEQUENCE: 6

Asp Ile Lys Met Thr Gln Ser Pro Ser Phe Leu Ser Ala Ser Val Gly
1               5                   10                  15

Asp Arg Val Thr Leu Asn Cys Lys Ala Ser Gln Asn Ile Asp Lys Tyr
            20                  25                  30
```

```
Leu Asn Trp Tyr Gln Gln Lys Leu Gly Glu Ser Pro Lys Leu Leu Ile
         35                  40                  45

Tyr Asn Thr Asn Asn Leu Gln Thr Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Phe Cys Leu Gln His Ile Ser Arg Pro Arg
                 85                  90                  95

Thr Phe Gly Gly Gly Thr His Leu Thr Val Leu Gly Gln Pro Lys Ala
             100                 105                 110

Ser Pro Ser Val Thr Leu Phe Pro Pro Ser Ser Glu Glu Leu Gly Ala
         115                 120                 125

Asn Lys Ala Thr Leu Val Cys Leu Ile Ser Asp Phe Tyr Pro Ser Gly
 130                 135                 140

Val Thr Val Ala Trp Lys Ala Asp Gly Ser Pro Ile Thr Gln Gly Val
145                 150                 155                 160

Glu Thr Thr Lys Pro Ser Lys Gln Ser Asn Asn Lys Tyr Ala Ala Ser
                 165                 170                 175

Ser Tyr Leu Ser Leu Thr Pro Asp Lys Trp Lys Ser His Ser Ser Phe
             180                 185                 190

Ser Cys Leu Val Thr His Glu Gly Ser Thr Val Glu Lys Lys Val Ala
         195                 200                 205

Pro Ala Glu Cys Ser
         210

<210> SEQ ID NO 7
<211> LENGTH: 456
<212> TYPE: PRT
<213> ORGANISM: Artificial Sequence
<220> FEATURE:
<223> OTHER INFORMATION: VET279 VH-CH

<400> SEQUENCE: 7

Glu Val Lys Leu Leu Glu Ser Gly Gly Gly Leu Val Gln Pro Gly Gly
 1               5                  10                  15

Ser Met Arg Leu Ser Cys Ala Gly Ser Gly Phe Thr Phe Thr Asp Phe
             20                  25                  30

Tyr Met Asn Trp Ile Arg Gln Pro Ala Gly Lys Ala Pro Glu Trp Leu
         35                  40                  45

Gly Phe Ile Arg Asp Lys Ala Lys Gly Tyr Thr Thr Glu Tyr Asn Pro
 50                  55                  60

Ser Val Lys Gly Arg Phe Thr Ile Ser Arg Asp Asn Thr Gln Asn Met
 65                  70                  75                  80

Leu Tyr Leu Gln Met Asn Thr Leu Arg Ala Glu Asp Thr Ala Thr Tyr
                 85                  90                  95

Tyr Cys Ala Arg Glu Gly His Thr Ala Ala Pro Phe Asp Tyr Trp Gly
             100                 105                 110

Gln Gly Thr Leu Val Thr Val Ser Ser Ala Ser Thr Thr Ala Pro Ser
         115                 120                 125

Val Phe Pro Leu Ala Pro Ser Cys Gly Thr Thr Ser Gly Ala Thr Val
 130                 135                 140

Ala Leu Ala Cys Leu Val Leu Gly Tyr Phe Pro Glu Pro Val Thr Val
145                 150                 155                 160

Ser Trp Asn Ser Gly Ala Leu Thr Ser Gly Val His Thr Phe Pro Ser
                 165                 170                 175

Val Leu Gln Ala Ser Gly Leu Tyr Ser Leu Ser Ser Met Val Thr Val
```

```
                    180                 185                 190
Pro Ser Ser Arg Trp Leu Ser Asp Thr Phe Thr Cys Asn Val Ala His
                195                 200                 205
Pro Pro Ser Asn Thr Lys Val Asp Lys Thr Val Arg Lys Thr Asp His
210                 215                 220
Pro Pro Gly Pro Lys Pro Cys Asp Cys Pro Lys Cys Pro Pro Pro Glu
225                 230                 235                 240
Met Leu Gly Gly Pro Ser Ile Phe Ile Phe Pro Pro Lys Pro Lys Asp
                245                 250                 255
Thr Leu Ser Ile Ser Arg Thr Pro Glu Val Thr Cys Leu Val Val Asp
                260                 265                 270
Leu Gly Pro Asp Asp Ser Asp Val Gln Ile Thr Trp Phe Val Asp Asn
                275                 280                 285
Thr Gln Val Tyr Thr Ala Lys Thr Ser Pro Arg Glu Glu Gln Phe Asn
                290                 295                 300
Ser Thr Tyr Arg Val Val Ser Val Leu Pro Ile Leu His Gln Asp Trp
305                 310                 315                 320
Leu Lys Gly Lys Glu Phe Lys Cys Lys Val Asn Ser Lys Ser Leu Pro
                325                 330                 335
Ser Pro Ile Glu Arg Thr Ile Ser Lys Asp Lys Gly Gln Pro His Glu
                340                 345                 350
Pro Gln Val Tyr Val Leu Pro Pro Ala Gln Glu Glu Leu Ser Arg Asn
                355                 360                 365
Lys Val Ser Val Thr Cys Leu Ile Glu Gly Phe Tyr Pro Ser Asp Ile
                370                 375                 380
Ala Val Glu Trp Glu Ile Thr Gly Gln Pro Glu Pro Glu Asn Asn Tyr
385                 390                 395                 400
Arg Thr Thr Pro Pro Gln Leu Asp Ser Asp Gly Thr Tyr Phe Leu Tyr
                405                 410                 415
Ser Arg Leu Ser Val Asp Arg Ser Arg Trp Gln Arg Gly Asn Thr Tyr
                420                 425                 430
Thr Cys Ser Val Ser His Glu Ala Leu His Ser His Thr Gln Lys
                435                 440                 445
Ser Leu Thr His Ser Pro Gly Lys
    450                 455

<210> SEQ ID NO 8
<211> LENGTH: 217
<212> TYPE: PRT
<213> ORGANISM: Artificial Sequence
<220> FEATURE:
<223> OTHER INFORMATION: VET158 VL-CL

<400> SEQUENCE: 8

Asp Ile Lys Met Thr Gln Ser Pro Ser Phe Leu Ser Ala Ser Val Gly
1               5                   10                  15
Asp Arg Val Thr Leu Asn Cys Lys Ala Ser Gln Asn Ile Asp Lys Tyr
                20                  25                  30
Leu Asn Trp Tyr Gln Gln Lys Leu Gly Glu Ser Pro Lys Leu Leu Ile
            35                  40                  45
Tyr Asn Thr Asn Asn Leu Gln Thr Gly Ile Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Val Ala Thr Tyr Phe Cys Leu Gln His Ile Ser Arg Pro Arg
                85                  90                  95
```

-continued

```
Thr Phe Gly Thr Gly Thr Lys Leu Glu Ile Lys Arg Ser Asp Ala Gln
            100             105             110

Pro Ser Val Phe Leu Phe Gln Pro Ser Leu Asp Glu Leu His Thr Gly
        115             120             125

Ser Ala Ser Ile Val Cys Ile Leu Asn Asp Phe Tyr Pro Lys Glu Val
    130             135             140

Asn Val Lys Trp Lys Val Asp Gly Val Val Gln Asn Lys Gly Ile Gln
145             150             155             160

Glu Ser Thr Thr Glu Gln Asn Ser Lys Asp Ser Thr Tyr Ser Leu Ser
            165             170             175

Ser Thr Leu Thr Met Ser Ser Thr Glu Tyr Gln Ser His Glu Lys Phe
            180             185             190

Ser Cys Glu Val Thr His Lys Ser Leu Ala Ser Thr Leu Val Lys Ser
        195             200             205

Phe Asn Arg Ser Glu Cys Gln Arg Glu
    210             215
```